United States Patent
Deininger et al.

(10) Patent No.: US 11,224,753 B1
(45) Date of Patent: Jan. 18, 2022

(54) MEDICAL DEVICES INCLUDING CONNECTOR ENCLOSURES WITH FEEDTHROUGH PASSAGEWAYS

(71) Applicant: MEDTRONIC, INC., Minneapolis, MN (US)

(72) Inventors: Steven T. Deininger, Blaine, MN (US); Jeffrey J. Clayton, Ramsey, MN (US); Charles E. Peters, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/487,291

(22) Filed: Sep. 28, 2021

Related U.S. Application Data

(63) Continuation of application No. 17/027,487, filed on Sep. 21, 2020, which is a continuation of application
(Continued)

(51) Int. Cl.
*A61N 1/375* (2006.01)
*A61N 1/37* (2006.01)
(Continued)

(52) U.S. Cl.
CPC ............ *A61N 1/3752* (2013.01); *B23K 26/24* (2013.01); *B23K 26/32* (2013.01); *A61N 1/3718* (2013.01);
(Continued)

(58) Field of Classification Search
None
See application file for complete search history.

(56) References Cited

U.S. PATENT DOCUMENTS

| 3,808,478 A | 4/1974 | Winkler |
| 4,127,134 A | 11/1978 | Ushakoff |

(Continued)

FOREIGN PATENT DOCUMENTS

| EP | 2667936 B1 | 8/2017 |
| EP | 2667938 B1 | 3/2018 |

(Continued)

OTHER PUBLICATIONS

International Patent Application No. PCT/US2011/065824, International Search Report and Written Opinion dated Jan. 10, 2012, 8 pages.

(Continued)

*Primary Examiner* — Michael W Kahelin
(74) *Attorney, Agent, or Firm* — Fredrikson & Byron, P.A.

(57) ABSTRACT

Medical devices provide metallic connector enclosures. The metallic connector enclosures may be constructed with relatively thin walls in comparison to polymer connector enclosures to aid in miniaturizing the medical device. The metallic connector enclosures may be constructed with interior surfaces that deviate less from an ideal inner surface shape in comparison to polymer connector enclosures to allow for better concentricity of electrical connectors. The metallic connector enclosures may include a panel that allows access to the cavity of the connector enclosure where set screw blocks, lead connectors, spacers, seals, and the like may be located. Furthermore, the lead connectors within the metallic connector enclosures may be separated from the metallic connector enclosure by being positioned within non-conductive seals that reside within features included in cavity walls of the connector enclosure. Similarly, set screw blocks may be separated from the metallic connector enclosure by non-conductive spacers present within the cavity.

20 Claims, 11 Drawing Sheets

Related U.S. Application Data

No. 15/885,243, filed on Jan. 31, 2018, now Pat. No. 10,780,284, which is a continuation of application No. 15/613,263, filed on Jun. 5, 2017, now Pat. No. 9,907,964, which is a continuation of application No. 15/210,645, filed on Jul. 14, 2016, now Pat. No. 9,669,228, which is a continuation of application No. 14/865,458, filed on Sep. 25, 2015, now Pat. No. 9,393,431, which is a continuation of application No. 13/976,401, filed as application No. PCT/US2011/065858 on Dec. 19, 2011, now Pat. No. 9,144,689.

(60) Provisional application No. 61/427,717, filed on Dec. 28, 2010.

(51) Int. Cl.
*B23K 26/24* (2014.01)
*B23K 26/32* (2014.01)
*B23K 101/36* (2006.01)
*B23K 103/14* (2006.01)

(52) U.S. Cl.
CPC ...... *B23K 2101/36* (2018.08); *B23K 2103/14* (2018.08); *Y10T 29/49117* (2015.01)

(56) References Cited

U.S. PATENT DOCUMENTS

| | | |
|---|---|---|
| 4,173,745 A | 11/1979 | Saunders |
| 4,254,775 A | 3/1981 | Langer |
| 4,296,390 A | 10/1981 | Vanderheyden et al. |
| 4,514,782 A | 4/1985 | Sakamoto et al. |
| 4,715,380 A | 12/1987 | Harris |
| 4,991,582 A | 2/1991 | Byers et al. |
| 4,995,389 A | 2/1991 | Harris |
| 5,032,692 A | 7/1991 | Devolder |
| 5,040,091 A | 8/1991 | Yamaoka et al. |
| 5,176,136 A | 1/1993 | Giele |
| 5,336,246 A | 8/1994 | Dantanarayana |
| 5,470,345 A | 11/1995 | Hassler et al. |
| 5,751,539 A | 5/1998 | Stevenson et al. |
| 5,769,874 A | 6/1998 | Dahlberg |
| 5,814,090 A | 9/1998 | Latterell et al. |
| 5,871,514 A | 2/1999 | Wiklund et al. |
| 5,905,627 A | 5/1999 | Brendel et al. |
| 6,083,640 A | 7/2000 | Lee et al. |
| 6,118,672 A | 9/2000 | Yamauchi et al. |
| 6,144,866 A | 11/2000 | Miesel et al. |
| 6,248,080 B1 | 6/2001 | Miesel et al. |
| 6,272,382 B1 | 8/2001 | Faltys et al. |
| 6,297,943 B1 | 10/2001 | Carson |
| 6,414,835 B1 | 7/2002 | Wolf et al. |
| 6,459,935 B1 | 10/2002 | Piersma |
| 6,498,951 B1 | 12/2002 | Larson et al. |
| 6,498,952 B2 | 12/2002 | Imani et al. |
| 6,505,073 B2 | 1/2003 | Gramse |
| 6,529,103 B1 | 3/2003 | Brendel et al. |
| 6,566,978 B2 | 5/2003 | Stevenson et al. |
| 6,643,903 B2 | 11/2003 | Stevenson et al. |
| 6,660,116 B2 | 12/2003 | Wolf et al. |
| 6,721,602 B2 | 4/2004 | Engmark et al. |
| 6,765,779 B2 | 7/2004 | Stevenson et al. |
| 6,850,405 B1 | 2/2005 | Mileham et al. |
| 6,852,925 B2 | 2/2005 | Wolf et al. |
| 6,895,276 B2 | 5/2005 | Kast et al. |
| 6,936,899 B2 | 8/2005 | Juengling |
| 6,975,906 B2 | 12/2005 | Rusin et al. |
| 6,986,453 B2 | 1/2006 | Jiang et al. |
| 6,987,428 B2 | 1/2006 | Marketkar et al. |
| 7,035,076 B1 | 4/2006 | Stevenson |
| 7,035,077 B2 | 4/2006 | Brendel |
| 7,113,387 B2 | 9/2006 | Stevenson et al. |
| 7,187,535 B1 | 3/2007 | Iyer et al. |
| 7,187,974 B2 | 3/2007 | Haeg et al. |
| 7,236,829 B1 | 6/2007 | Farazi et al. |
| 7,242,982 B2 | 7/2007 | Singhal et al. |
| 7,306,490 B1 | 12/2007 | Jeter |
| 7,317,946 B2 | 1/2008 | Twetan et al. |
| 7,363,090 B2 | 4/2008 | Halperin et al. |
| 7,425,142 B1 | 9/2008 | Putz |
| 7,515,964 B1 | 4/2009 | Alexander et al. |
| 7,551,960 B2 | 6/2009 | Forsberg et al. |
| 7,553,193 B2 | 6/2009 | Kast et al. |
| 7,590,450 B2 | 9/2009 | Iyer et al. |
| 7,594,828 B2 | 9/2009 | Alexander et al. |
| 7,630,768 B1 | 12/2009 | Coffed et al. |
| 7,647,110 B2 | 1/2010 | Hrnfeldt et al. |
| 7,647,111 B2 | 1/2010 | Ries et al. |
| 7,668,597 B2 | 2/2010 | Engmark et al. |
| 7,693,576 B1 | 4/2010 | Lavie et al. |
| 7,725,177 B2 | 5/2010 | Iyer |
| 7,725,190 B2 | 5/2010 | Iyer et al. |
| 7,736,191 B1 | 6/2010 | Sochor |
| 7,748,093 B2 | 7/2010 | Iyer et al. |
| 7,765,005 B2 | 7/2010 | Stevenson |
| 7,774,066 B2 | 8/2010 | Deininger et al. |
| 7,798,862 B2 | 9/2010 | Kast et al. |
| 7,801,613 B2 | 9/2010 | Li et al. |
| 7,803,014 B2 | 9/2010 | Sprain et al. |
| 7,839,620 B2 | 11/2010 | Iyer et al. |
| 7,917,218 B2 | 3/2011 | Iyer et al. |
| 7,955,543 B2 | 6/2011 | Deininger et al. |
| 8,041,427 B2 | 10/2011 | Kast et al. |
| 8,131,368 B2 | 3/2012 | Kast et al. |
| 8,131,369 B2 | 3/2012 | Taylor et al. |
| 8,154,846 B2 | 4/2012 | Fauer et al. |
| 8,162,684 B1 | 4/2012 | Sochor |
| 8,401,648 B2 | 3/2013 | Kast et al. |
| 8,494,649 B2 | 7/2013 | Stancer et al. |
| 8,554,329 B1 | 10/2013 | Mann et al. |
| 8,593,816 B2 | 11/2013 | Iyer et al. |
| 8,604,341 B2 | 12/2013 | Barry et al. |
| 8,620,449 B2 | 12/2013 | Zhao et al. |
| 8,781,589 B1 | 7/2014 | Jiang et al. |
| 8,903,473 B2 | 12/2014 | Rogers et al. |
| 9,138,587 B2 | 9/2015 | Deininger et al. |
| 9,138,588 B2 | 9/2015 | Deininger et al. |
| 9,138,821 B2 | 9/2015 | Brosnan et al. |
| 9,144,689 B2 | 9/2015 | Deininger et al. |
| 9,221,119 B2 | 12/2015 | Schmidt |
| 9,278,223 B2 | 3/2016 | Kast et al. |
| 9,393,431 B2 | 7/2016 | Deininger et al. |
| 9,403,022 B2 | 8/2016 | Ries et al. |
| 9,409,031 B2 | 8/2016 | Lindner et al. |
| 9,572,993 B2 | 2/2017 | Deininger et al. |
| 9,597,518 B2 | 3/2017 | Deininger et al. |
| 9,669,228 B2 | 6/2017 | Deininger et al. |
| 9,675,807 B2 | 6/2017 | Schmidt |
| 9,855,436 B2 | 1/2018 | Dearden et al. |
| 10,143,849 B2 | 12/2018 | Deininger et al. |
| 10,195,448 B2 | 2/2019 | Deininger et al. |
| 10,224,518 B2 | 3/2019 | Freitag et al. |
| 10,335,603 B2 | 7/2019 | Lindner et al. |
| 10,646,719 B2 | 5/2020 | Deininger et al. |
| 10,780,284 B2 | 9/2020 | Deininger et al. |
| 2002/0107554 A1 | 8/2002 | Biggs et al. |
| 2002/0138114 A1 | 9/2002 | Gramse |
| 2002/0165588 A1 | 11/2002 | Fraley et al. |
| 2003/0139096 A1 | 7/2003 | Stevenson et al. |
| 2003/0163171 A1 | 8/2003 | Kast et al. |
| 2004/0034393 A1 | 2/2004 | Hansen et al. |
| 2004/0176815 A1 | 9/2004 | Janzig et al. |
| 2004/0201947 A1* | 10/2004 | Stevenson ............ A61N 1/3754 361/302 |
| 2004/0220627 A1 | 11/2004 | Crespi et al. |
| 2004/0260354 A1 | 12/2004 | Nielsen et al. |
| 2005/0203583 A1 | 9/2005 | Twetan et al. |
| 2006/0009813 A1 | 1/2006 | Taylor et al. |
| 2006/0015150 A1 | 1/2006 | Rusin et al. |
| 2006/0089680 A1 | 4/2006 | Bruchmann et al. |
| 2006/0161204 A1 | 7/2006 | Colvin et al. |
| 2006/0212087 A1 | 9/2006 | Haller et al. |
| 2007/0203530 A1 | 8/2007 | Hubing et al. |

(56) References Cited

U.S. PATENT DOCUMENTS

| | | |
|---|---|---|
| 2007/0239223 A1 | 10/2007 | Engmark et al. |
| 2007/0248881 A1 | 10/2007 | Scott et al. |
| 2008/0033500 A1 | 2/2008 | Strother et al. |
| 2008/0065181 A1 | 3/2008 | Stevenson |
| 2008/0246231 A1 | 10/2008 | Sjostedt et al. |
| 2008/0262563 A1 | 10/2008 | Sjostedt |
| 2009/0059468 A1 | 3/2009 | Iyer |
| 2009/0076353 A1 | 3/2009 | Carpenter et al. |
| 2009/0192578 A1 | 7/2009 | Biggs |
| 2009/0246617 A1 | 10/2009 | Howard et al. |
| 2009/0270940 A1 | 10/2009 | Deininger et al. |
| 2010/0009512 A1 | 1/2010 | Fishburn |
| 2010/0038132 A1 | 2/2010 | Kinney et al. |
| 2010/0177458 A1 | 7/2010 | Iyer |
| 2010/0318156 A1 | 12/2010 | Edgell et al. |
| 2011/0015694 A1 | 1/2011 | Alexander et al. |
| 2011/0029028 A1 | 2/2011 | Peters et al. |
| 2011/0147062 A1 | 6/2011 | Stevenson |
| 2011/0160808 A1 | 6/2011 | Lyden et al. |
| 2012/0035616 A1 | 2/2012 | Olsen et al. |
| 2012/0053646 A1 | 3/2012 | Brase et al. |
| 2012/0193141 A1 | 8/2012 | Reisinger et al. |
| 2012/0203292 A1 | 8/2012 | Deininger et al. |
| 2012/0203314 A1 | 8/2012 | Deininger et al. |
| 2014/0043739 A1 | 2/2014 | Deininger et al. |
| 2014/0049924 A1 | 2/2014 | Deininger et al. |
| 2017/0087358 A9 | 3/2017 | Deininger et al. |
| 2017/0087359 A9 | 3/2017 | Deininger et al. |
| 2017/0157405 A1 | 6/2017 | Deininger et al. |
| 2018/0015290 A1 | 1/2018 | Deininger et al. |
| 2018/0175566 A1 | 6/2018 | Hanson et al. |
| 2019/0143123 A1 | 5/2019 | Deininger et al. |
| 2019/0314634 A1 | 10/2019 | Deininger et al. |
| 2019/0358459 A1 | 11/2019 | Baade et al. |
| 2019/0366099 A1 | 12/2019 | Deininger et al. |

FOREIGN PATENT DOCUMENTS

| | | |
|---|---|---|
| JP | 2009531832 A | 9/2009 |
| WO | 2007109762 A1 | 9/2007 |
| WO | 2008088568 A1 | 7/2008 |
| WO | 2008100319 A1 | 8/2008 |
| WO | 2009045809 A2 | 4/2009 |
| WO | 2010081139 A1 | 7/2010 |
| WO | 2010117842 A1 | 10/2010 |

OTHER PUBLICATIONS

International Patent Application No. PCT/US2011/065845, International Search Report and Written Opinion dated Feb. 19, 2013, 13 pages.

International Patent Application No. PCT/US2011/065858, International Search Report and Written Opinion dated Jun. 29, 2012, 14 pages.

* cited by examiner

MEDICAL DEVICES INCLUDING CONNECTOR ENCLOSURES WITH FEEDTHROUGH PASSAGEWAYS

This present application claims priority to and is a continuation of U.S. patent application Ser. No. 17/027,487, filed Sep. 21, 2020, which claims priority to and is a continuation of U.S. patent application Ser. No. 15/885,243, filed Jan. 31, 2018, now U.S. Pat. No. 10,780,284, issued Sep. 22, 2020, which claims priority to and is a continuation of U.S. patent application Ser. No. 15/613,263, filed Jun. 5, 2017, now U.S. Pat. No. 9,907,964, issued Mar. 6, 2018, which claims priority to and is a continuation of U.S. patent application Ser. No. 15/210,645, filed Jul. 14, 2016, now U.S. Pat. No. 9,669,228, issued Jun. 6, 2017, which claims priority to and is a continuation of U.S. patent application Ser. No. 14/865,458, filed Sep. 25, 2015, now U.S. Pat. No. 9,393,431, issued Jul. 16, 2016, which claims priority to and is a continuation of U.S. patent application Ser. No. 13/976,401, filed Sep. 17, 2013, now U.S. Pat. No. 9,144,689, issued Sep. 29, 2015, which claims priority to and is a § 371 National Phase of International Patent Application No. PCT/US2011/065858, filed Dec. 19, 2011, which claims priority to U.S. Provisional Patent Application No. 61/427,717, filed Dec. 28, 2010. Each of these applications are incorporated herein by reference in their entirety.

TECHNICAL FIELD

Embodiments relate to medical devices that have connector enclosures that receive medical leads. More particularly, embodiments relate to medical devices that have metallic connector enclosures.

BACKGROUND

Medical devices including those that may be implanted and those that are worn externally on the body of the patient utilize medical leads to carry signals between circuitry within the medical device and electrodes on distal ends of the medical leads. The medical leads may be used to deliver electrical stimulation pukes from the medical circuitry to the tissue and/or to sense physiological signals from the tissue and convey those signals to the medical circuitry.

Typically, the medical lead is a separate item from the medical device. The lead is routed within the body of the patient to the area where stimulation or sensing is to occur. A proximal end of the lead is connected to the medical device by inserting the lead into a connector enclosure of the medical device. The connector enclosure establishes electrical contact between electrical connectors on the lead and corresponding lead connectors within the connector enclosure. The connector enclosure may provide seals that engage the medical lead and prevent body fluids from entering into the connector enclosure of the medical device.

The connector enclosure of the medical device is often a polymer which is formed over the lead connectors and lead frames that provide a conductor from the electrical connector to electrical contacts on the base of the connector enclosure. The medical device also includes a hermetically sealed can that, is typically constructed of a metal such as titanium. The can has feedthrough pins exiting a top of the can that are attached to the electrical contacts of the connector enclosure during assembly of the medical device to complete the electrical pathways from the medical circuitry to the lead connectors of the connector enclosure.

The polymer connector enclosure may have various drawbacks. For instance, the polymer connector enclosure typically requires a significant volume to provide adequate strength. The polymer wall thicknesses are necessarily large enough to adequately support the lead connectors and lead frames present within the connector enclosure, which may inhibit the ability to further miniaturize the medical device. Furthermore, the inner surfaces of the connector enclosure that engage the lead connectors have a relatively large deviation from an ideal inner surface shape. These deviations cause the longitudinal sequence of lead connectors to have relatively large variations in concentricity, which leads to a relatively large lead insertion force and that, contributes to lead damage during insertion.

SUMMARY

Embodiments address issues such as these and others by provide a medical device that has a metallic connector enclosure. The inherent strength of the metal allows the connector enclosure to be made with relatively thin walls to aid in miniaturization of the medical device. Furthermore, the precision that is achievable when creating the inner surfaces of the connector enclosure such as by machining allows the deviation from an ideal shape to be relatively small to better align components so as to aid in reducing insertion force. To allow access to the interior of the connector enclosure for assembly purposes, a cavity may be created with an open urea that can be covered by a panel that is bonded in place. Furthermore, to isolate lead connectors from the metallic connector enclosure, non-conductive lead connector spacers may be included within the cavity of the metallic connector enclosure.

Embodiments provide a method of constructing a medical device. The method involves providing a can that houses medical circuitry and providing electrical connectors within the can and electrically connected to the medical circuitry. The method farther involves providing a metallic connector enclosure comprising a metallic body defining a cavity and a metallic panel welded to the metallic body and covering the cavity, the body including an opening to the cavity. The method involves providing lead connectors within the cavity and in alignment with the opening, the lead connectors being positioned between the metallic body and the metallic panel and providing electrical conductors that are electrically connected to the lead connectors within the cavity and that are electrically isolated from the metallic connector enclosure while being exposed outside of the metallic connector enclosure. The method involves placing a portion of the can in contact with a metallic edge of the metallic connector enclosure such that the electrical connectors within the can and the electrical conductors exposed outside the metallic connector enclosure are in contact and are contained by a housing created by the contact of the can and the metallic connector enclosure and creating a bond at the contact of the portion of the can and the metallic edge of the metallic connector enclosure.

Embodiments provide a method of constructing a medical device. The method involves providing a can that houses medical circuitry and providing electrical connectors within the can and electrically connected to the medical circuitry. The method further involves providing a metallic connector enclosure defining a cavity and including an opening to the cavity, the metallic connector enclosure including walls with portions of at least one wall having a thickness of 25 thousandths of an inch or less. The method involves providing lead connectors within the cavity and in alignment with the opening and providing electrical conductors that are electrically connected to the lead connectors within the cavity and that are electrically isolated from the metallic connector enclosure while being exposed outside of the metallic connector enclosure. The method involves placing a portion of the can in contact with a metallic edge of the metal lie connector enclosure such that the electrical connectors within the can and the electrical conductors exposed outside the metallic connector enclosure are in contact and are contained by a housing created by the contact of the can and the metallic connector enclosure and creating a bond at the contact of the portion of the can and the metallic edge of the metallic connector enclosure.

Embodiments provide a method of constructing a medical device. The method involves providing a can that houses medical circuitry and providing electrical connectors within the can and electrically connected to the medical circuitry. The method farther involves providing a metallic connector enclosure having internal walls defining a cavity with the metallic connector enclosure including an opening to the cavity. The method farther involves providing a plurality of lead connectors within the cavity and in alignment with the opening, each of the lead connectors being surrounded by a seal, each of the seals separating the lead connectors from the internal walls where a centerline of each lead connector varies by 8 thousandths of an inch or less from the centerline of every other lead connector. The method involves providing electrical conductors that are electrically connected to the lead connectors within the cavity and that are electrically isolated from the metallic connector enclosure while being exposed outside of the metallic connector enclosure. The method involves placing a portion of the can in contact with a metallic edge of the metallic connector enclosure such that the electrical connectors within the can and the electrical conductors exposed outside the metallic connector enclosure are in contact and are contained by a housing created by the contact of the can and the metallic connector enclosure and creating a bond at the contact of the portion of the can and the metallic edge of the metallic connector enclosure.

Embodiments provide a method of constructing a medical device. The method involves providing a can that houses medical circuitry and providing electrical, connectors within the can and electrically connected to the medical circuitry. The method further involves providing a metallic connector enclosure comprising a metallic body defining a cavity, the body including an opening to the cavity, the cavity having a recess and providing non conductive lead connector spacers within the recess. The method further involves providing lead connectors within the cavity and in alignment with the opening, the lead connectors being disposed within the non-conductive lead connector spacers and providing electrical conductors that are electrically connected to the lead connectors within the cavity and that are electrically isolated from the metallic connector enclosure while being exposed outside of the metallic connector enclosure. The method involves placing a portion of the can in contact with a metallic edge of the metallic connector enclosure such that the electrical connectors within the can and the electrical conductors exposed outside the metallic connector enclosure are in contact and are contained by a housing created by the contact of the can and the metallic connector enclosure and creating a bond at the contact of the portion of the can and the metallic edge of the metallic connector enclosure.

Embodiments provide a medical device that includes a can that houses medical circuitry and electrical connectors within the can and electrically connected to the medical circuitry. The medical device includes a metallic connector enclosure comprising a metallic body defining a cavity and a metallic panel welded to the metallic body and covering the cavity, the body including an opening to the cavity. The medical device includes lead connectors within the cavity and in alignment with the opening, the lead the connectors being positioned between the metallic body and the metallic panel, and includes electrical conductors that are electrically connected to the lead connectors within the cavity and that are electrically isolated from the metallic connector enclosure while being exposed outside of the metallic connector enclosure. A portion of the can is in contact with a metallic edge of the metallic connector enclosure such that the electrical connectors within the can and the electrical conductors exposed outside the metallic connector enclosure are in contact and are contained by a housing created by the contact of the can and the metallic connector enclosure, and a bond is present at the contact of the portion of the cats and the metallic edge of the metallic connector enclosure.

Embodiments provide a medical device that includes a can that houses medical circuitry and electrical connectors within the can and electrically connected to the medical circuitry. The medical device includes a metallic connector enclosure defining a cavity and including an opening to the cavity, the metallic connector enclosure including walls with portions of at least one wall having a thickness of 25 thousandths of an inch or less. The medical device includes lead connectors within the cavity and in alignment with the opening and electrical conductors that are electrically connected to the lead connectors within the cavity and that are electrically isolated from the metallic connector enclosure while being exposed outside of the metallic connector enclosure. A portion of the can is in contact with a metallic edge of the metallic connector enclosure such that the electrical connectors within the can and the electrical conductors exposed outside the metallic connector enclosure are in contact and are contained by a housing created by the contact of the can and the metallic connector enclosure, and a bond is present at the contact of the portion of the can and the metallic edge of the metallic connector enclosure.

Embodiments provide a medical device that includes a can that houses medical circuitry and electrical connectors within the can and electrically connected to the medical circuitry. The medical device further includes a metallic connector enclosure having internal walls defining a cavity with the metallic connector enclosure including an opening to the cavity. The medical device further includes a plurality of lead connectors within the cavity and in alignment with the opening, each of the lead connectors being surrounded by a seal, each of the seals separating the lead connectors from the internal walls where a centerline of each lead connector varies by 8 thousandths of an inch or less from the centerline of every other lead connector. The medical device includes electrical conductors that are electrically connected to the lead connectors within the cavity and that are electrically isolated from the metallic connector enclosure while being exposed outside of the metallic connector enclosure. A portion of the can is in contact with a metallic edge of the metallic connector enclosure such that the electrical connectors within the can and the electrical conductors exposed outside the metallic connector enclosure are in contact and are contained by a housing created by the contact of the can and the metallic connector enclosure, and a bond is present at the contact of the portion of the can and the metallic edge of the metallic connector enclosure.

Embodiments provide a medical device that includes a can that houses medical circuitry and an electrical connector within the can and electrically connected to the medical circuitry. The medical device includes a metallic connector enclosure comprising a metallic body defining a cavity, the body including tut opening to the cavity, the cavity having a recess and a non-conductive lead connector spacer within the recess. The medical device includes a lead connector within the cavity and in alignment with the opening, the lead connector being disposed within the non-conductive lead connector seal and an electrical conductor that is electrically connected to the lead connector within the cavity and that is electrically isolated from the metallic connector enclosure while being exposed outside of the metallic connector enclosure. A portion of the can is in contact with a metallic edge of the metallic connector enclosure such that the electrical connector within the can and the electrical conductor exposed outside the metallic connector enclosure are in contact and are contained by a housing created by the contact of the can and the metallic connector enclosure, and a bond is present at the contact of the portion of the can and the metallic edge of the metallic connector enclosure.

DETAILED DESCRIPTION

Embodiments provide for medical devices that have a can housing medical circuitry and have a connector enclosure with a metallic weld to the can. In one or more embodiments, the metallic weld provides a relatively strong attachment between the connector enclosure and the can even where medical adhesive is not used to aid in attaching the connector enclosure to the can. In one or more embodiments the metallic weld provides a hermetic seal for the can. Furthermore, in one or more embodiments, the connector enclosure may have a relatively small size such as where the can omits barbs, pins, straps, and other features ordinarily used to attach a connector enclosure to a can.

Figure 1:
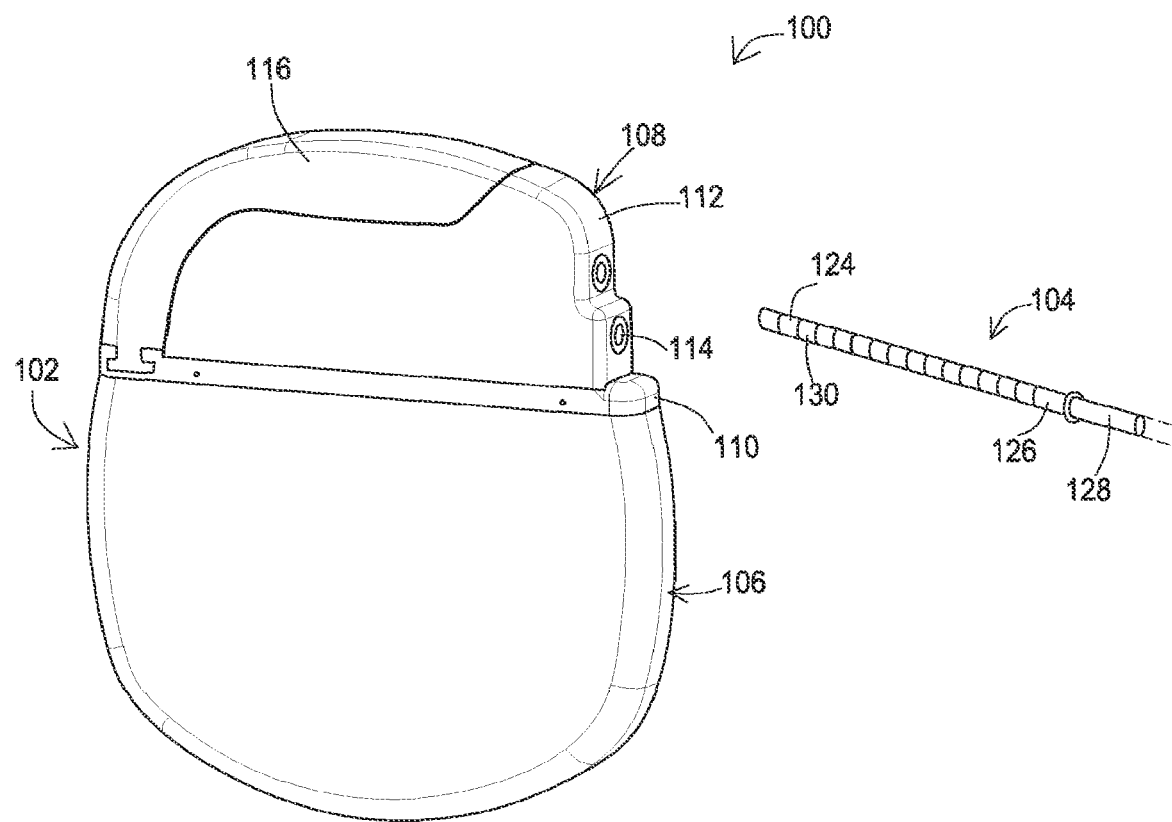
FIG. 1 shows a front perspective view of a medical system includes a medical device example according to various embodiments and a medical lead.

FIG. 1 shows an example of a medical system 100 that includes an embodiment of a medical device 102 and a corresponding medical lead 104. The medical device 102 includes a can 106 that houses medical circuitry and also includes a connector enclosure 108 that is attached to the can 106 and houses the electrical connections to the lead 104. The connector enclosure 108 includes one or more openings 114 that receive the proximal end of the medical lead 104. The connector enclosure 108 of this particular example includes a connector enclosure body 112 where the openings 114 are located and a connector enclosure base 110 upon which the connector enclosure body 112 is mounted. An antenna cover 116 that may be constructed of materials such as polysulfone or polyurethane is mounted atop the connector enclosure 108 as the antenna cover 116 resides atop the connector enclosure body 112.

Figure 2:
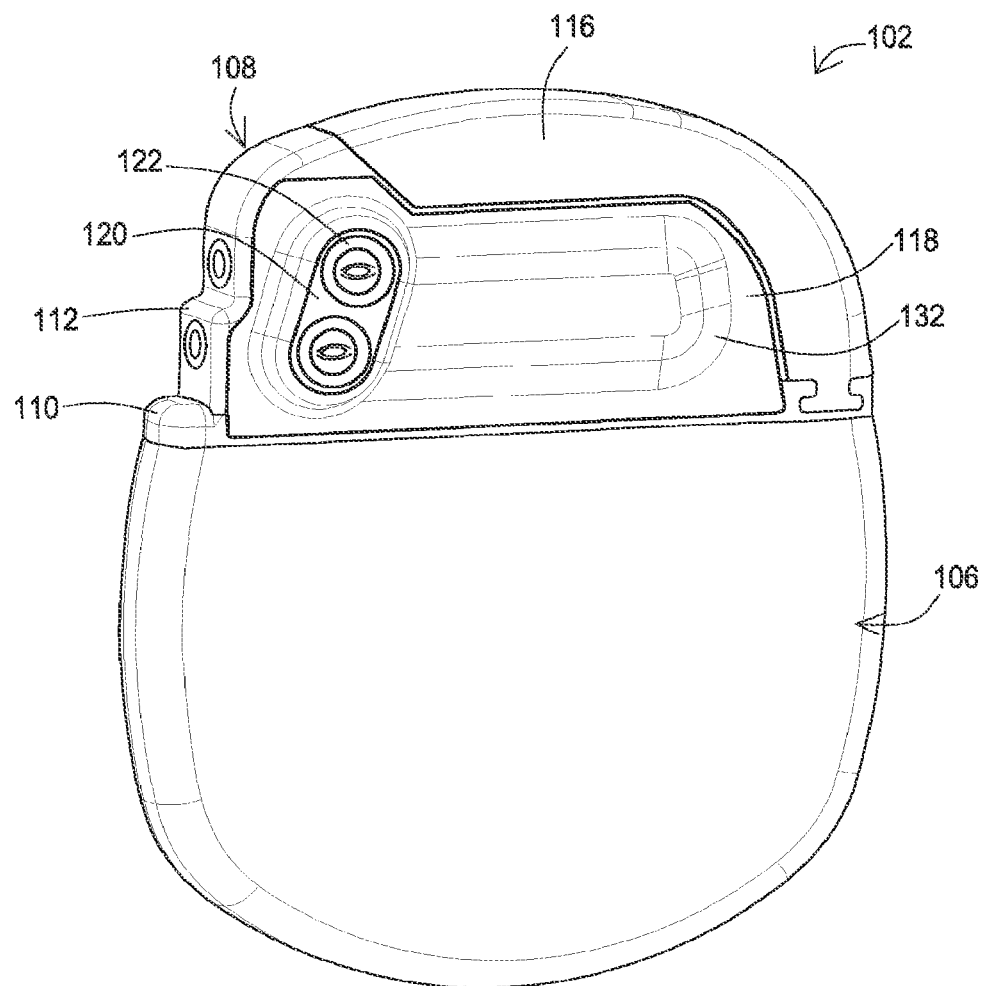
FIG. 2 shows a rear perspective view of the medical device example.

As shown in FIG. 2, the connector enclosure 108 may also include additional features. For instance, a connector enclosure panel 118 covers a cavity within the connector enclosure body 112 which is discussed in more detail below. In this particular example, the panel 118 includes an outwardly protruding region 132 that accommodates items located within the cavity being covered by the panel 118. Also in this example, a seal 120 that is constructed of a material such as liquid silicone rubber or a medical adhesive creates a seal between the screw block and grommet covered set screws 122 are present.

A set screw block discussed below is present within the set screw block spacer, also discussed below, that underlies the seal 120 where the openings 114 lead to passages in the set screw block. The lead 104 passes through the passages in the set screw block, and a clink 126 of the lead 104 resides within the set screw blocks upon full insertion of the lead 104. The set screw 122 is tightened against the clink 126 to secure the lead 104 within the connector enclosure 108. Thus, the set screw block within the spacer 180 may also act as a lead connector. Conventional seals may be present within the openings 114 to seal against the clink 126 and resist the entry of bodily fluids into the openings 114.

The medical lead 104 includes a lead body 128 typically constructed of a polymer followed by the metal clink 126 and then an alternating series of non conductive spacers 130 typically constructed of a polymer and electrical connectors 124 that are typically metal. The electrical connectors 124 and in some examples the clink 126 are connected to electrical conductors within the lead body 128 that extend to a distal end where electrodes are present at the stimulation/sensing site. Upon insertion of the lead 104 into the connector enclosure 108, the electrical connectors 124 align with lead connectors that are electrically connected to the medical circuitry within the can 106.

In the example shown in FIGS. 1-11, it may be desirable that the connector enclosure 108 be bonded to the can 106 by a metallic weld. In that case, at least a top edge of the can 106 is a metal such as various grades of titanium while at least a bottom edge of the connector enclosure 108 is also a metal such as various grades of titanium. In the example shown, the entire can 106 is a metal such as grade 5 titanium while at least the connector enclosure base 110 of the connector enclosure 108 is also entirely a metal such as grade 5 titanium.

Figure 3:
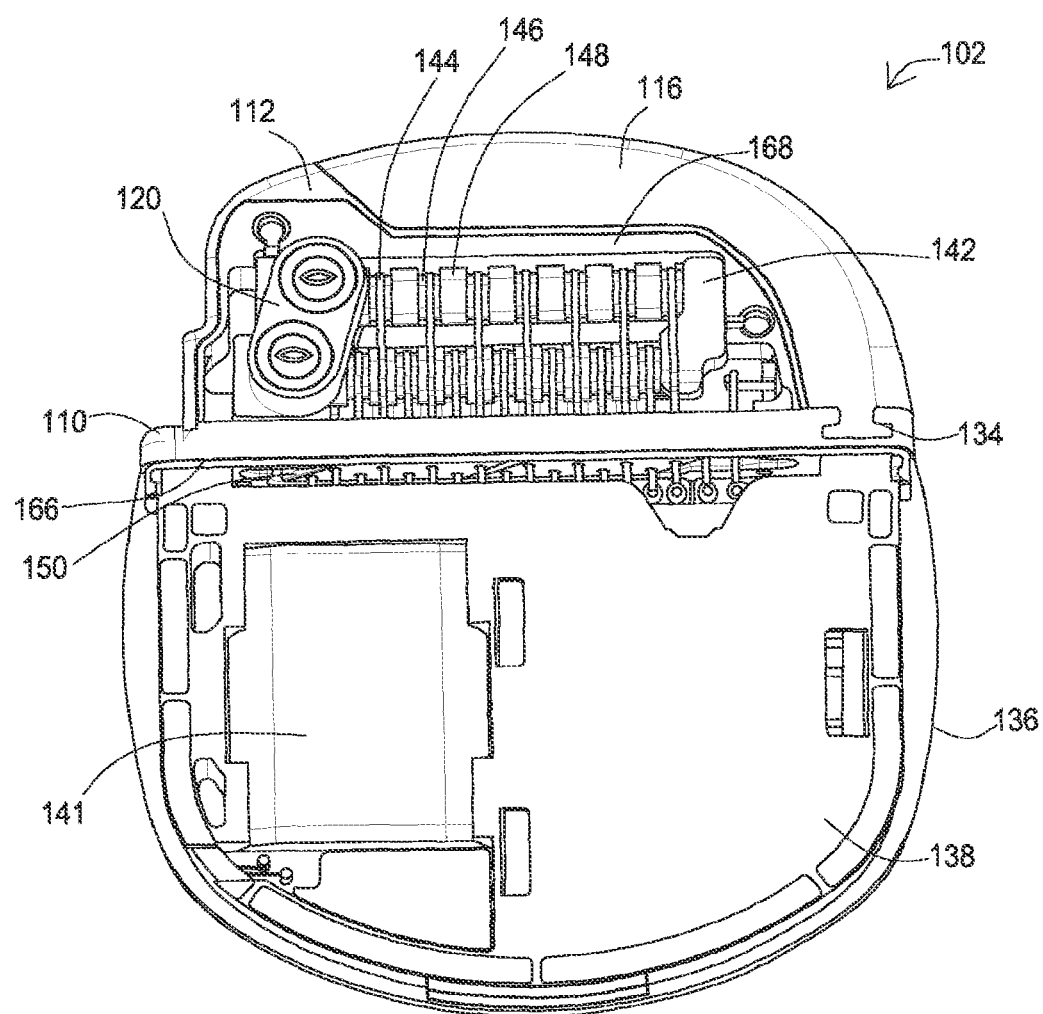
FIG. 3 shows a rear view of the medical device example with a rear portion of a can and a rear panel removed.
Figure 4:
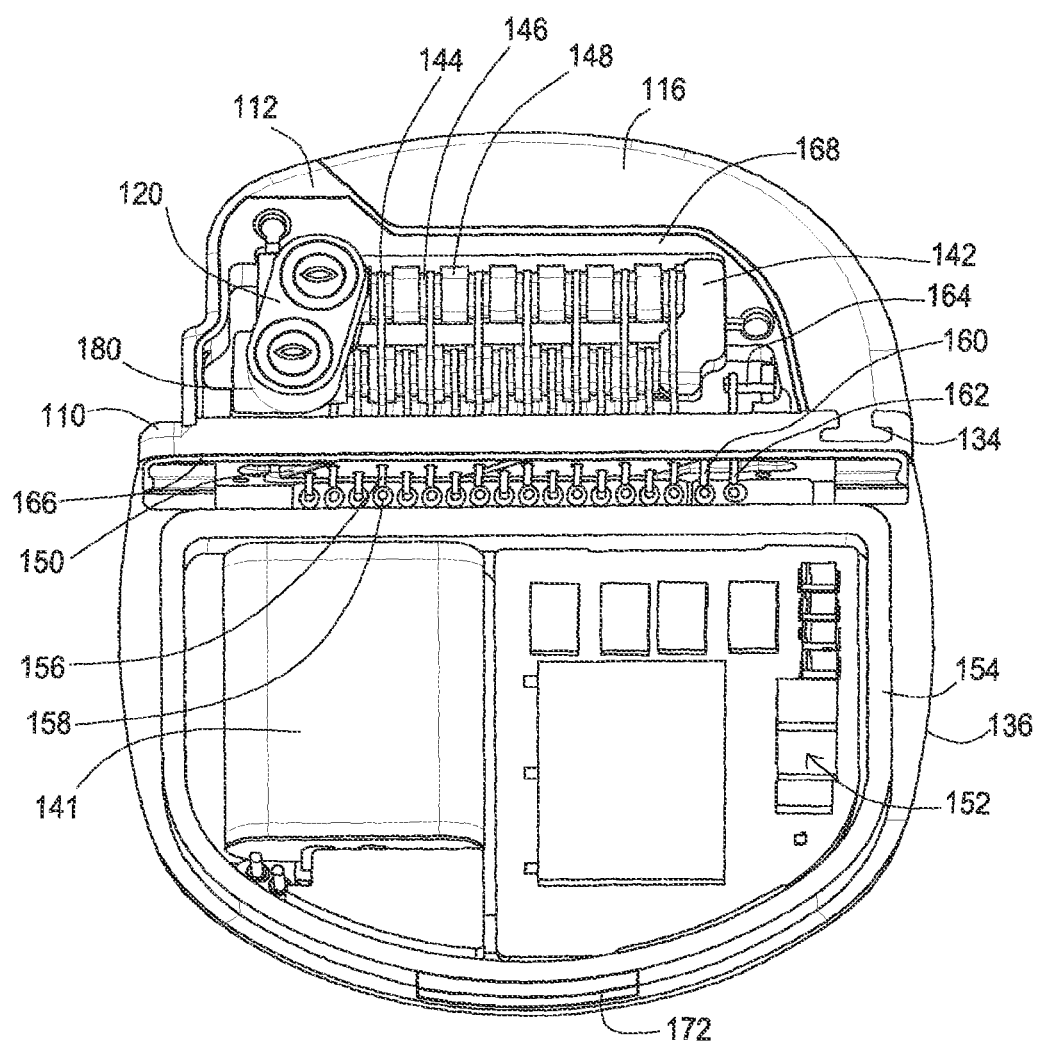
FIG. 4 shows a rear view of the medical device example with an isolation cup removed.

As shown in FIGS. 3 and 4, wherein a tear half of the can 106 is removed for purposes of illustration while a front half 136 of the can 106 remains, the connector enclosure base 110 of this example includes a lower edge 166 of a lip that the upper edge of the can 106 resides against. Accordingly, the metallic weld, such as a laser seam weld, may be per formed along the lower edge 166 of the lip to create the bond between the connector enclosure base 110 and the can 106.

For embodiments where the bond is other than a metallic weld, such as where conventional mounting techniques and medical adhesives are used instead, the upper edge of the can 106 and/or the lower edge of the connector enclosure 108 may be materials other than metal.

The can 106 of this example also includes an open top. The connector enclosure base 110 mates to the open top with the top edge of the open top of the can 106 meeting the lower edge 166 of the lip on the connector enclosure base 110. Thus, the connector enclosure base 110 acts as a lid to close the open top of the can 106, and upon being metallically welded together, creates a hermetically sealed enclosure.

The panel 118 may be metallic as may be the connector enclosure body 112. Thus, where the connector enclosure base 110 is also metallic, particularly for embodiments where the connector enclosure 108 is bonded by a metallic weld to the can 106, the entire connector enclosure 108 may be metallic. For instance, the connector enclosure body 112 may be a grade 5 titanium while the panel 118 may be a grade 1 titanium that is stamped rather than machined, or a grade 5 titanium that, is also machined. An entirely metallic connector enclosure 108 may be relatively strong while being small and with relatively precise features as discussed in more detail below.

Where the connector enclosure 108 includes a metal connector enclosure base 110, a metal connector enclosure body 112, and a metal connector enclosure panel 118, each of these pieces may be welded, together to complete the enclosure. The bonds between the body 112, the base 110, and/or the panel 118 may alternatively be other than metallic welds particularly for embodiments where the body 112, the base 110, or the panel 118 is other than a metal. For instance, the bond between the body and the base 110 may utilize medical adhesive barbs, straps, and the like for embodiments where one or both of the base 110 and body 112 are not metal.

The panel 118 is removed for purposes of illustration in FIGS. 3 and 4, where the connector enclosure body 112 of this particular example includes a slight indention 168 within which tire panel 118 rests. Thus, the panel 118 may be bonded to the body 112 by a metallic weld such as a laser seam weld along the edge of the indention 168. Similar to the alternative bonds between the base 110 and the body 112, alternative manners of joining the panel 118 to the body 112 may also be used, such as medical adhesive barbs, straps, and the like, especially for embodiments where one or both of the panel 118 and body 112 are not metal.

During assembly of the connector enclosure 108, the panel 118 may be left aside while components are installed into the cavity within the connector enclosure body 112. These components may include the setscrew block spacer 180, a set of lead connectors 146, lead connector seals 148 disposed between the lead connectors 146, and end seals 142. Feedthrough pins 144 which are electrical conductors that carry individual electrical signals between the interior of the can 106 and the interior of the connector enclosure 108 may also be positioned within the cavity and bonded to the lead connectors 146 such as by a resistance weld or other weld.

Figure 10:
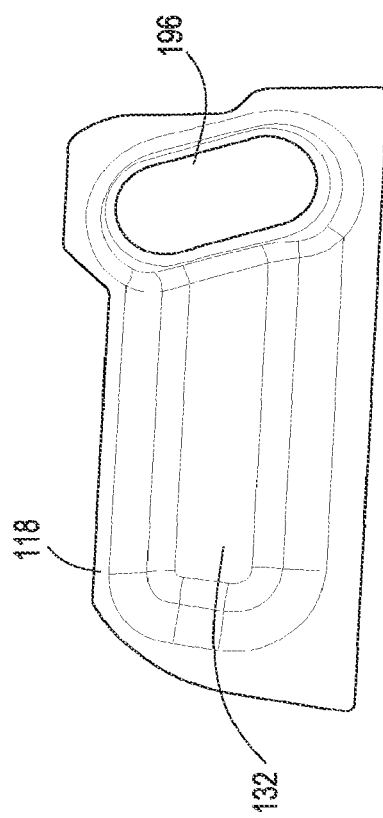
FIG. 10 shows an interior side of the panel of the connector enclosure.

The feedthrough pins 144 exit the connector enclosure 108 via feedthrough passageway 200 within the connector enclosure base 110 as shown in FIG. 10. These feedthrough passageways 200 may provide a seal against the feedthrough pins 144, as show in FIG. 6, by including ferrules 178 that the feedthrough pins 144 pass through that are filled with a glass or other non-conductor 176 that creates a seal and also gives the feedthrough pins a fixed position relative to the base 110. This seal to the feedthrough pins 144 allows the can 106 to achieve the hermetic seal upon the connector enclosure base 110 being mounted and bonded to the can 106.

Figure 5:
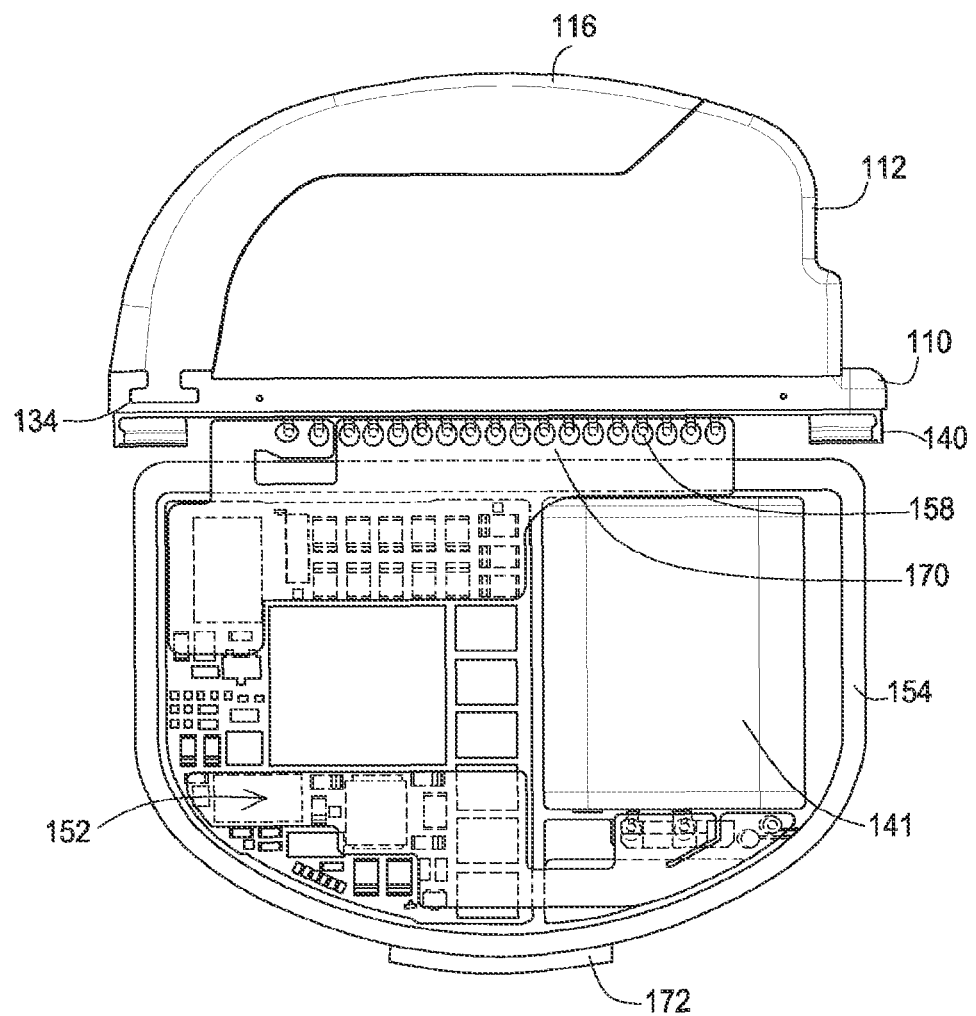
FIG. 5 shows a front view of the medical device example with the can removed.

As shown in FIGS. 4 and 5, the exposed tip 156 of the feedthrough pins 144 are bonded to electrical contacts 158 of a flexible circuit connector 170 winch is shown transparently for purposes of illustration. The flexible circuit connector 170 extends down to meet electrical connections of medical circuitry 152. The medical circuitry 152 may include such items as a microcontroller device, a memory device, stimulation capacitor, a telemetry device, a battery 141, and the like.

As shown in FIG. 3, the medical circuitry 152 is contained within an isolation cup 138 that is constructed of a material such as a liquid crystal polymer, polypropylene, and the like and that is removed for purposes of illustration in FIGS. 4 and 5. The isolation cup 138 fits within the can 106 and may have a physical connection to the connector enclosure base 110. For instance, in some embodiments the connector enclosure base 110 may include feet 140 as shown in FIG. 5, and the isolation cup 138 may have an interference or snap fit to the feet 140. A desiccant may also be present within the can 106 such as within a pocket of the isolation cup 138, while a rubber bumper 172 or bumper of other similar material may be present within the can 106 below the isolation cup 138 so that the isolation cup 138 comes to rest in a fixed and supported position within the can 106.

As shown in FIGS. 4 and 5, a coil assembly 154 may be included together with the medical circuitry 152 within the isolation cup 138. This coil assembly 154 may be used for various purposes. For instance, the coil assembly 154 may be used to receive recharge energy and/or provide near field telemetry. The coil assembly 154 may include a coil housing that is constructed of a material such as a liquid crystal polymer, polypropylene, and the like with the coil wound within the housing.

The coil assembly 154 and the frequency at which the coil assembly 154 operates are less affected by surrounding metal than the telemetry antenna so the coil assembly 154 is included within the can 106 of this embodiment. The telemetry antenna is positioned atop the connector enclosure 108 where it is not surrounded by metal, as discussed further below in relation to FIG. 7. Consequently, in this particular embodiment, the coil assembly 154 and the telemetry antenna are physically separated from one another. However, it will be appreciated that where the coil assembly 154 and the telemetry antenna operate in frequency bands that are significantly spaced from one another, the physical separation between the two is less a factor when using both simultaneously.

In the particular example shown in FIG. 4, the connector enclosure base 110 provides an integrated filtered feedthrough utilizing monolithic capacitors. One or more filter plates 150 are attached to the underside of the connector enclosure base 110 such as by medical adhesive, soldering, and the like. In this example, the filter plates 150 are constructed of ceramic with wire traces present within the ceramic that establish electrical continuity with the feedthrough pins 144 while also establishing capacitance within the conductive path of the traces. The wire traces of the filter plates 150 are electrically coupled to the connector enclosure base 110 by soldering of the edges of the filter plates 150 for embodiments where the connector enclosure base 110 is metal to effectively ground the feedthrough capacitors to the base 110, as well as to the can 106 for embodiments where the connector enclosure base 110 is welded or otherwise conductively attached to the can 106.

Figure 6:
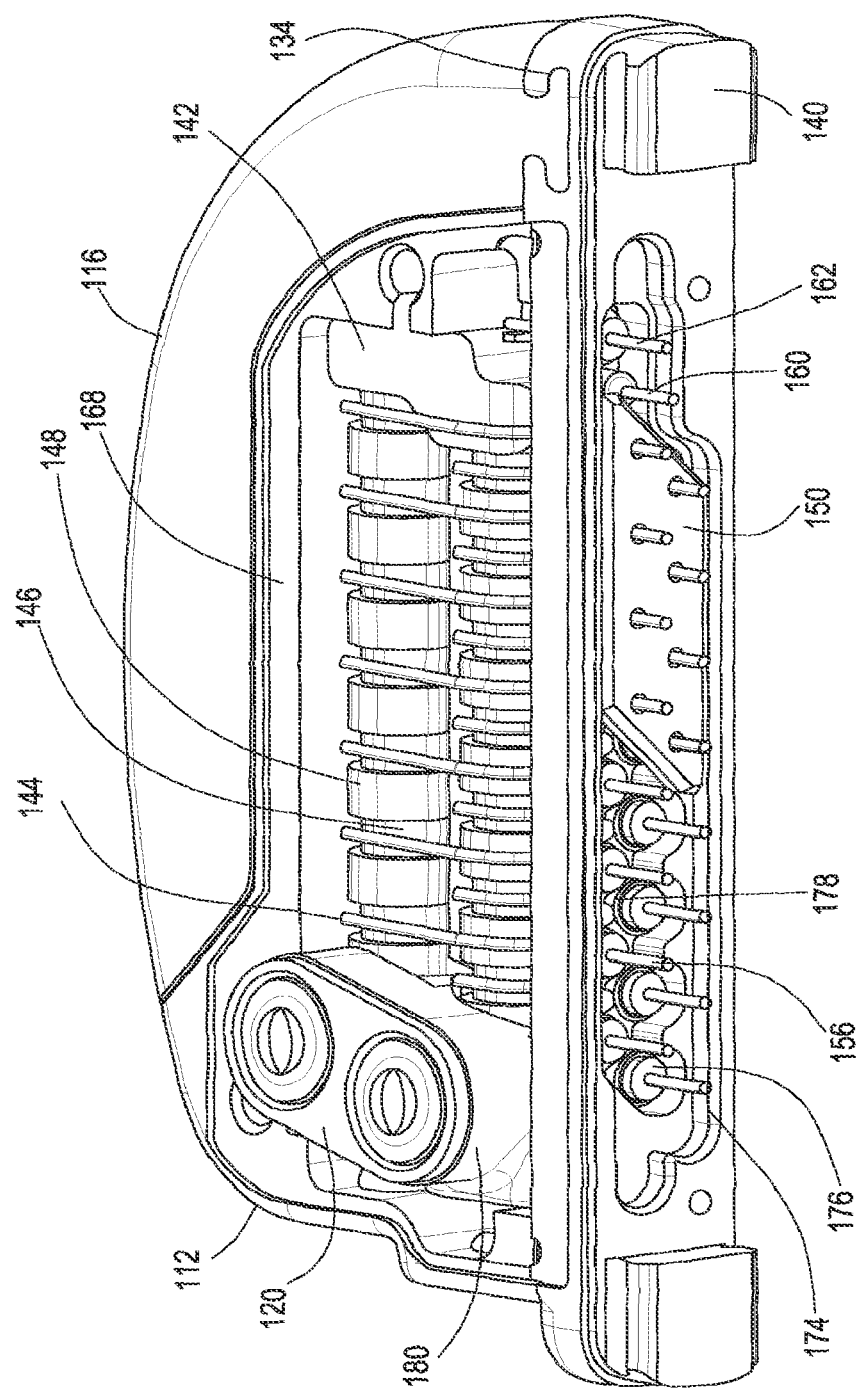
FIG. 6 shows a bottom perspective view of a connector enclosure example of the medical device with the panel removed.

As can be seen in FIG. 6, the connector enclosure base 110 of this example includes a recessed area 174 which provides a location for installation of the biter plates 150. FIG. 6 and FIG. 4 also show a ground pin 160 that is present within the connector enclosure base 110. This ground pin 160 also electrically connects to the flexible circuit connector 170 to provide a ground connection for the medical circuitry 152. The ground pin 160 is then welded or otherwise bonded to the connector enclosure base 110 for embodiments where the connector enclosure base 110 is a metal to thereby establish the ground with the body of the patient and the metallic portions of the cats 106.

Figure 7:
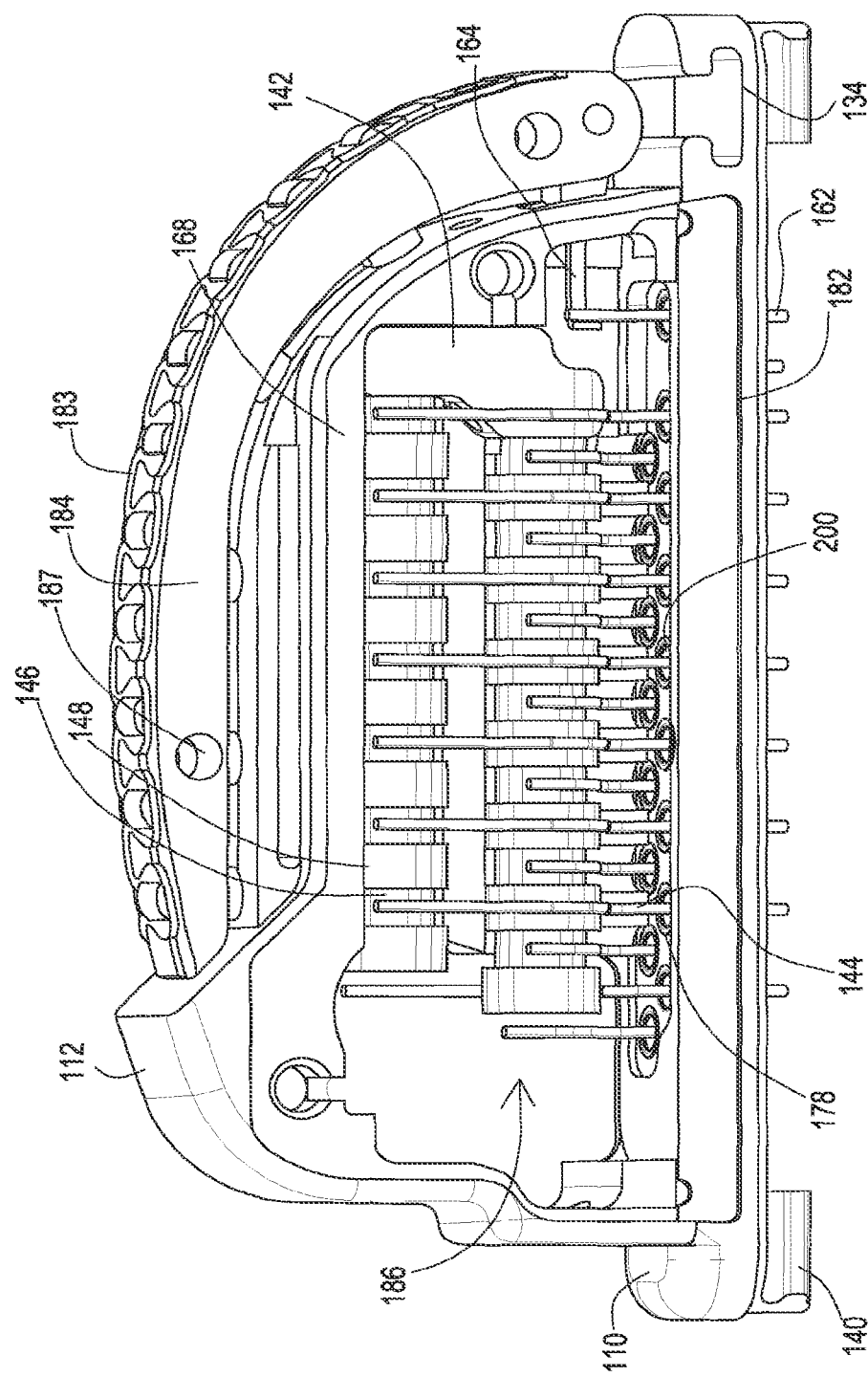
FIG. 7 shows a top perspective view of the connector enclosure example of the medical device with an antenna support cover removed.

Additionally, for embodiments where a telemetry antenna 183 as seen in FIG. 7 is provided atop the connector enclosure 108, an antenna pin 162 may be included that passes through the connector enclosure base 110 and connects to the flexible circuit connector 170. As shown in FIG. 6, the antenna pin 162 may be isolated from the base 110 via a ferrule filled with a glass or other non-conductor as with the other feedthrough pins 144. However, the antenna pin 162 is not filtered by the filter plates 150 so that the telemetry signals are not subject to attenuation from the capacitive filters of the filter plates 150. A connecting portion 164 of the antenna 183 as shown FIGS. 4 and 7 may then connect the amentia pin 162 to the antenna conductor present within the 183 cover 116. The connecting portion 164 may be an integral section of the conductor forming the telemetry antenna 183 as shown in FIG. 7 or may be a separate conductor bridging the telemetry antenna 183 to the antenna pin 162.

The connector enclosure base 110 may include features to aid in the construction of the medical device 102. For instance, the connector enclosure base 110 may provide the feet 140 that extend into the isolation cup 138 to provide a snug fit of the isolation cup 138 to the connector enclosure base 110 prior to the connector enclosure base 110 being bonded to the cart 106. Additionally, in this example where the telemetry antenna 183 is positioned atop the connector enclosure 108, the connector enclosure base 110 includes a slot 134 that receives a foot of the antenna cover 116 to aid in holding the antenna cover 116 and the antenna 183 within the antenna cover 116 in place.

FIG. 7 provides a view of the feedthrough pins 144 passing through the feedthrough passageways 200 that include the ferrules 178 from a top perspective. Here, it can be seen that the lead connectors 146 are positioned in longitudinal alignment with corresponding feedthrough passageways 200 of the enclosure base 110. This longitudinal alignment allows the feedthrough pins 144 to be straight in the longitudinal dimension which facilitates assembly and reduces feedthrough pin length. The feedthrough pins 144 of this example have bends in the transverse dimension which allows the feedthrough pins 144 to mount to the lead connectors 146 at the outer sides while returning to a more central location where the feedthrough passageways 200 are located. This configuration aids in assembling the stacked configuration of lead bores us shown.

In this particular example, the lead connectors 146 for a top lead passageway am offset in the longitudinal direction relative to the lead connectors 146 for a bottom lead passageway. This allows the feedthrough pins 144 for the lead connectors 146 of the top lead passageway to pass by the non-conductive lead connector seals 148 for the lead connectors 146 of the bottom lead passageway. In this manner, the feedthrough pins 144 of the top lead passageway do not interfere with the lead connectors 146 or feedthrough pins 144 of the bottom lead passageway. Furthermore, the feedthrough pins 144 are spaced from the walls of the cavity formed in the connector enclosure body 112 which may be metal so that the electrical signals are not short circuited to ground and are not attenuated to a degree that might affect operation of the medical device 102.

FIG. 7 also provides a view of the cavity within the connector enclosure 108 where the set screw block spacer 180 is removed for purposes of illustration to reveal a recess 186 of the cavity that is machined or otherwise manufactured to have inner surfaces that accommodate and secure the set screw block spacer 180. This spacer 180 may be constructed of a non-conductive rigid material such as polysulfone which may directly contact metal walls of the cavity within the connector enclosure body 112 while supporting the set screw blocks and isolating the set screw blocks from the metal walls so that electrical signals are not short circuited to ground and are not attenuated to a degree that might affect operation of the medical device 102. Other machined or otherwise manufactured inner surface features are discussed further below with reference to FIG. 5).

To ensure that the seal 120 will properly adhere to the set screw block spacer 180, the set screw block spacer 180 may be manufactured such as by applying a coating of siloxane. The siloxane layer may then be primerized with a layer of silicone medical adhesive which may be diluted with a heptanes solvent. The seal 120 may then be applied atop the medical adhesive printer layer, such as by applying liquid silicone rubber to form the seal 120.

FIG. 7 also shows an antenna support 184 that the antenna conductor 183 may rest upon or be encased by, and the antenna support 184 lies within the antenna cover 116 which has also been removed for purposes of illustration, in this particular example, the connector enclosure body 112 includes an arced top upon which the antenna cover 116 rests. The antenna support 184, which may be constructed of materials such as polysulfone, polyurethane, and the like, isolates the antenna conductor 183 from the connector enclosure body 112, which is particularly of interest for embodiments that include a metallic connector enclosure body 112. The antenna support 184 may be coated in the same manner discussed above for the set screw block spacer 180 so that portions of the antenna support 184 that extend into the cavity of the cavity of the connector enclosure body 112 may adhere to the liquid silicone rubber that has been inserted into the cavity of the connector enclosure body 112.

The antenna cover 116 and/or the antenna support 184 may provide a sealed passageway for the connecting pin 164 to pass from, the portion of the cavity behind the end seal 142 to the interior of the antenna support 184 where contact with the antenna conductor 183 is made. The antenna support 184 includes suture holes 187 which align with suture holes that may also be included in the antenna cover lib that allow the medical device 102 to be sutured in place within the body of the patient.

The connector enclosure base 110 of this example includes a lip with an upper edge 182. The panel 118 rests at the upper edge 182 of the lip where a laser seam weld may be created to attach the bottom edge of the panel 118 to the upper edge 182 of the lip. As discussed above, the lower edge 166 of the lip on the connector enclosure base 110 rests against an upper edge of the can 106 where a laser seam weld may be created to attach the connector enclosure base 110 to the can 106.

Figure 8:
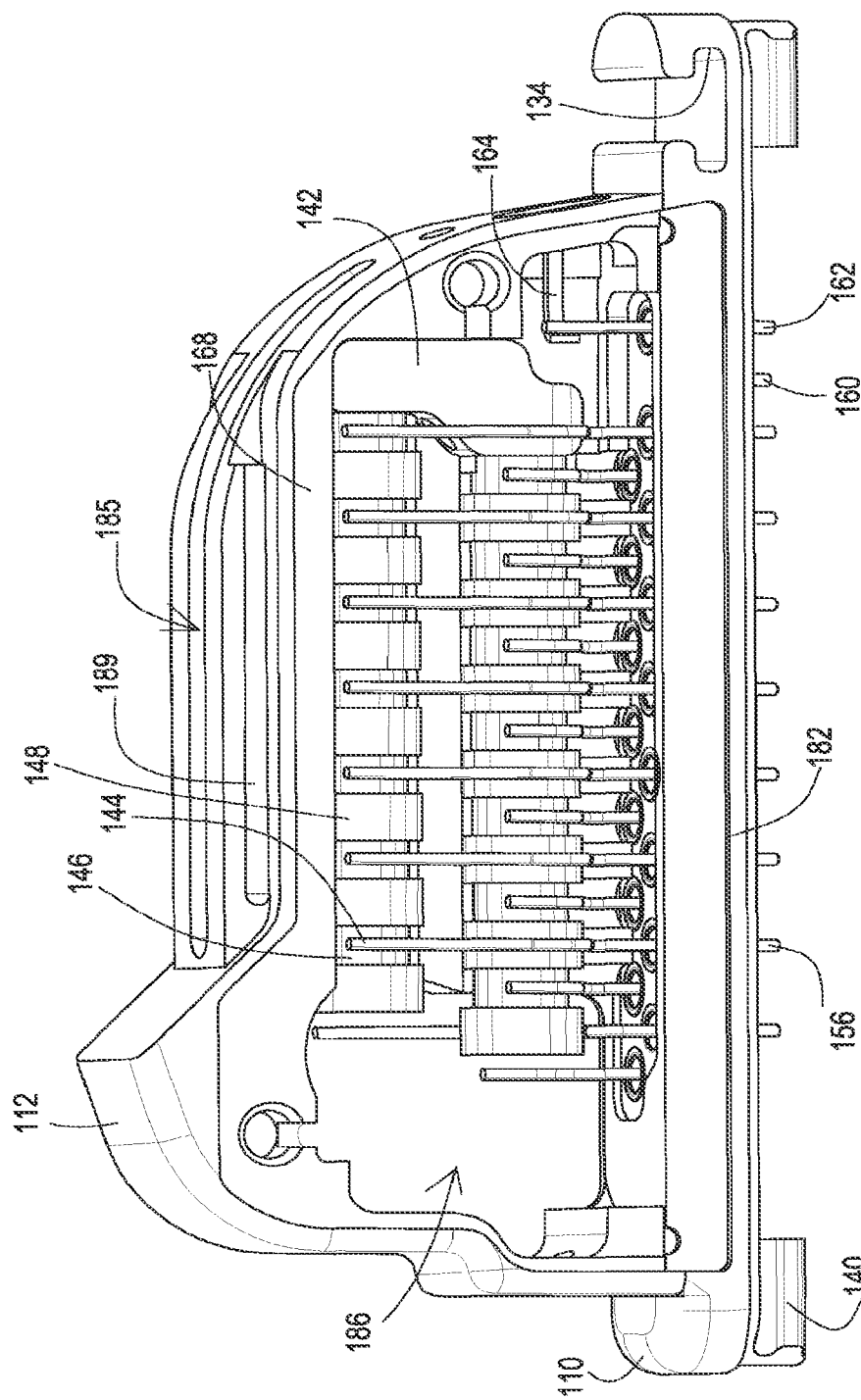
FIG. 8 shows a rear view of the connector enclosure example of the medical device with set screw blocks and a set screw spacer, a from seal, and an antenna support removed.

In FIG. 8, the antenna support 184 is removed for purposes of illustration. The outer surface 185 of the connector enclosure body 112 where the antenna cover 116 rests can be seen. The antenna cover 116 includes longitudinal ribs that slide into longitudinal grooves 180 formed into the top of the connector enclosure body 112. These grooves 189 hold the antenna cover 116, and hence the antenna support 184, in a fixed position relative to the connector enclosure body 112. The connector enclosure base 110 may be subsequently moved into position relative to the connector enclosure body 112 which involves placing the end of the antenna cover 116 into the slot 134 in the connector enclosure base 110. The slot 134 runs orthogonally to the grooves 180 such that the antenna cover 116 and antenna support 184 are locked in place on the connector enclosure 108.

Figure 9:
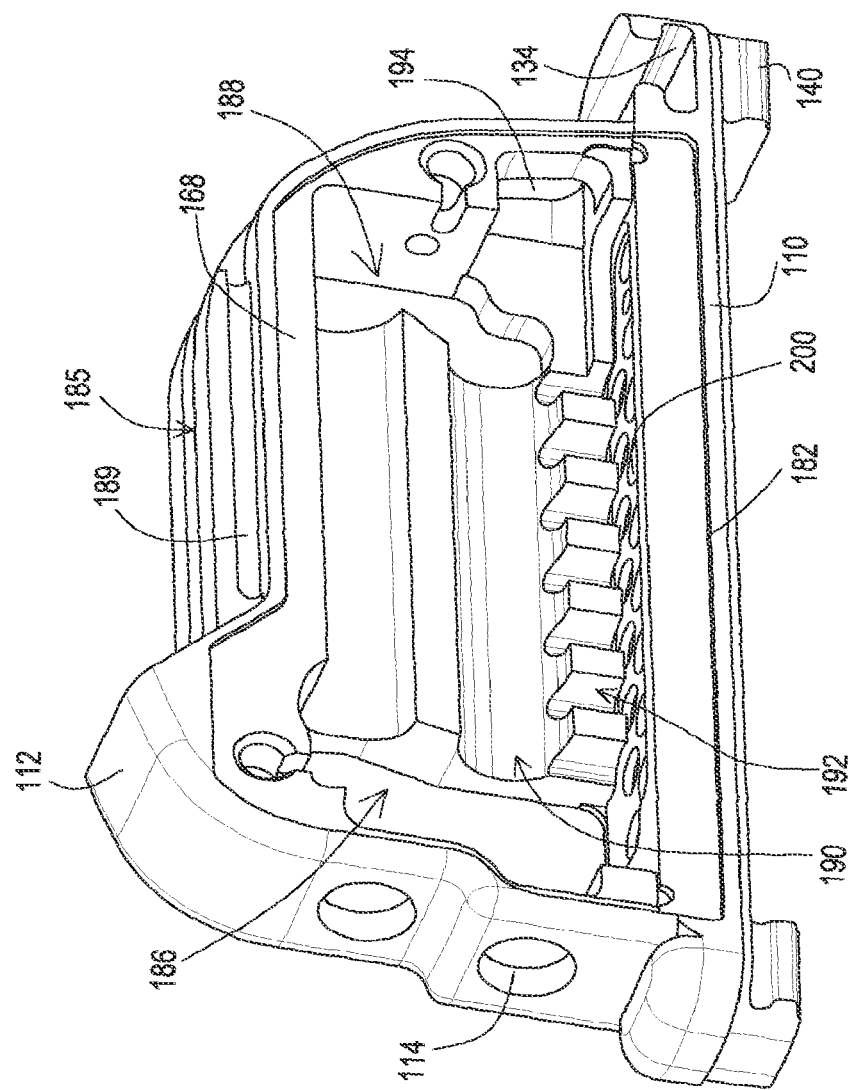
FIG. 9 shows a rear perspective view of the connector enclosure of the medical device with lead connectors, spacers, and feedthrough pins removed.

FIG. 9 shows the connector enclosure body 112 mounted to the connector enclosure base 110 but with all other components removed for purposes of illustration. The features of the interior walls within the cavity of the enclosure body 112 are in view. Considering that the connector enclosure body 112 and the interior walls of the cavity in particular may be constructed of metal, the features of the interior walls may be machined or otherwise manufactured to include a variety of features to accommodate the components that reside within the connector enclosure 108.

In this example, additional recesses 190 that accommodate, align, and secure the lead connectors 146 and lead connector seals 148 can be seen. The recesses 190 align with the openings 114 to provide longitudinal passageways where the lead connectors 146 and lead connector seals 148 are present as shown in the preceding figures to ultimately receive the leads 104.

As shown in FIG. 8, the lead connector seals 148, which may be constructed, of non-conductive materials such as liquid silicone rubber, urethane, and the like, operate as spacers to both separate the lead connectors 146 from the interior walls of the cavity formed in the connector enclosure body 112 and to separate one lead connector 146 from an adjacent lead connector. In one particular example, the lead connectors 146 may be canted coil spring connectors such as those available front the Bal Seal Engineering company.

The seals 148 may create various nearest edge to nearest edge spacing between the connectors 146, for instance from 16 thousandths of an inch for some embodiments to 33 thousandths of an inch for others. Furthermore, the seals 148 may create various spacing between the cavity walls and the nearest edge of the connectors 146, for instance from 10 thousandths of an inch for some embodiments to 15 thousandths of an inch for others. The non-conductive seals 148 effectively isolate the electrical connectors 146 from the metal walls and adjacent electrical connectors 146 so that electrical signals are not shorted to ground and are not attenuated to a degree that affects operation of the medical device 102.

The alignment of the lead connector seals 148 and the lead connectors 146 directly impact the amount of insertion force necessary to insert a lead 104. The proximal end of the lead 104 passes through each lead connector 146 until the lead 104 is fully inserted into the connector enclosure 108. As the proximal cud of the lead 104 approaches the fully inserted position, all lead connectors 546 of a given lead passageway are engaging the lead body and/or connectors 124. Each lead connector 146 thereby causes friction with the lead 104 during insertion which results in a given insertion force. The less the concentricity from one lead connector 146 to the next varies, the smaller live amount of insertion force required to insert the lead. A smaller amount of insertion force has a smaller likelihood of damaging the medical lead 104.

In the example shown in FIG. 9, the lead passageway recesses 190 are formed by machining or other precision method such that the centerline of each lead connector 146 in the longitudinal direction varies by 8 thousandths of an inch or less from the centerline of every other lead connector 146 in some embodiments, for instance 4 thousandths of an inch or less for embodiments with walls constructed of various grades of titanium or similar metals. For instance, the connector enclosure body 112 may be titanium and the recesses 190 may be machined into the titanium to provide this degree of concentricity for the lead connectors 146.

A recess 188 that accommodates and secures the end seal 142 can also be seen in FIG. 9. In this example, the end seal 142 shown in FIG. 8 is a double seal that captures the most proximal lead connector 146 for both the upper and the lower lead passageways. It will be appreciated that individual end seals could be used in place of a double seal for two lead passageways, such as where multiple recesses 188 may be present to accommodate and secure each end seal or where a single recess 188 as shown accommodates two individual end seals in a stacked configuration. The end seal 142, which may also be constructed of a non-conductive material such as a liquid silicone rubber, urethane, and the like, effectively isolates the final electrical connectors 146 front the metal walls so that electrical signals are not shorted to ground and are not attenuated to a degree that affects operation of the medical device 102.

In this example shown in FIG. 9, the connector enclosure body 112 also includes a set of recesses 192 that align with feedthrough passageways 200 in the connector enclosure base 110. These recesses allow the feedthrough pins 114 of that side of the connector enclosure body 112 to pass into the feedthrough passageways 200 without obstruction while retaining a robust lower support for the lead connector seals 148 of the lower lead passageway.

Where the connector enclosure body 112 is constructed of a material that is relatively sturdy, such as titanium or other biocompatible metals, the walls of the enclosure body 112 may be made relatively thin which allows for an overall reduction, in the volume of the connector enclosure 108. For instance, in this example where the connector enclosure body 112 is constructed of a metal such as titanium, the walls for the recesses 186 and 188 are the thinnest walls for the enclosure body 112 and may be machined or otherwise formed so that the thickness is on the order of 25 thousandths of an inch or less in some embodiments, such as 8 thousandths of an inch for various grades of titanium and similar metals. Other embodiments may provide for the thinnest, walls to be in other locations within the cavity in addition to or as an alternative to the recesses 186 and 188 having the thinnest walls.

In this embodiment where the telemetry antenna 183 sits atop the connector enclosure 112, the connecting pin 164 passes through a seal that is mounted within an opening 194 present within the connector enclosure body 112 to enter the antenna support 184. The antenna cover 116 may have the seal integrally formed so that upon mounting the antenna cover 116, the seal is disposed within the opening 194. In this particular example, the antenna pin 162 extends from the feedthrough passageway of the connect or enclosure base 110 into a region between the end seal 142 and the opening 194, as shown in FIG. 8. With the opening 194 on the end of the connector enclosure 108 opposite the lead passageway openings 114, the conduction path from the antenna pin 162 to the antenna 183 within the housing 184 avoids intersections with other feedthrough pins 144, lead connectors 146, set screw blocks, and the leads 104 themselves.

FIG. 10 shows the inner side of the connector enclosure panel 118. The panel 118 includes a peripheral surface that rests against the indention 168 of the connector enclosure body 112 once the panel 118 is bonded in place by a laser scam weld or other bond. The panel 118 of this embodiment includes the region 132 that is concave when viewed on the inner side as shown in FIG. 10. This region 132 accommodates the seals 148 and lead connectors 146 forming the lead passageways as well as the feedthrough pins 144 present between the seals 148 and the panel 118. This concavity allows the width of the connector enclosure body 112 to be less than the width needed for clearance in the region 132 to thereby reduce the overall volume of the connector enclosure 108.

The panel 118 also includes an opening 196 where the set screw block is exposed to insert the set screws and set screw grommets 122 into the set screw block and where the seal 120 can be added to seal the junction of the opening 196 and grommets to the set screw spacer and set screw block. The opening 196 of this embodiment is also present within a concavity that allows the connector enclosure body 112 to have a width that is less than the width needed for clearance of the set screw block spacer 180 to further reduce the overall volume of the connector enclosure 108.

Where the panel 118 as welded to the connector enclosure body 112, the panel 118 may be constructed of various biocompatible metals. For instance the panel 118 may be constructed of various grades of titanium such as grades 1 or 5. However, constructing the panel 118 of a grade 1 titanium allows the panel to be stamped more easily although the panel 118 may be manufactured in other ways such as by machining. The thickness of the panel 118 may be relatively small, similar to the thinnest walls of the connector enclosure base 112, because of the inherent strength in a metal panel 118. The panel 118 may have a thickness on the order of 25 thousandths of an inch or less for some embodiments that use metal, such as 8 to 12 thousandths of an inch for various grades of titanium and similar metals.

Figure 11:
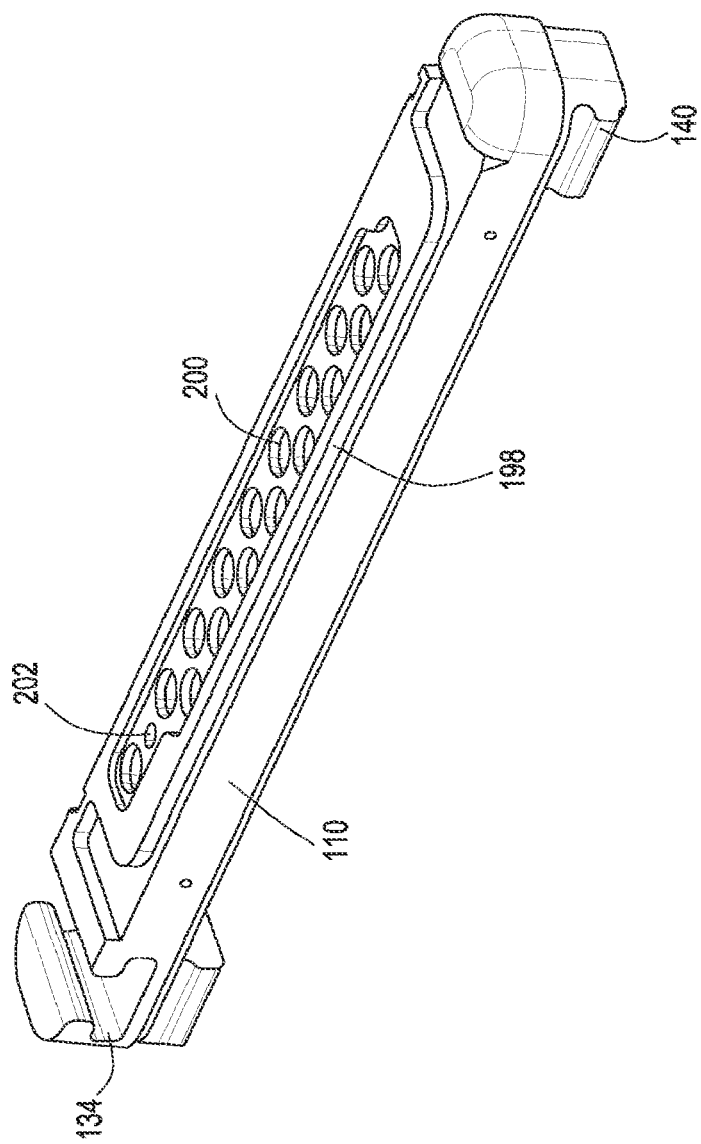
FIG. 11 shows a perspective view of a base of the connector enclosure.

FIG. 11 shows an example of the connector enclosure base 110 with other elements of the connector enclosure 108 removed. In this example, the connector enclosure base 110 includes an upper edge 198 of the lip where the connector enclosure body 112 may be seated and ultimately welded in place. The connector enclosure base 110 provides the feedthrough passageways 200 and also provides a ground pin passageway 202. The ground pin 160 terminates within the ground pin passageway 202 where it is welded to the connector enclosure base 110.

The connector enclosure base 110 may be constructed of various materials. For embodiments where the connector enclosure base 110 is welded to the top edge of the can 106 and/or welded to the connector enclosure body 112, the connector enclosure base 110 is constructed of a biocompatible metal. For instance, the connector enclosure base 110 may be constructed of grade 5 titanium that is machined to provide the features as shown.

One manner of assembling the example of the connector enclosure 108 shown in FIGS. 1-11 may proceed as follows. The connector enclosure base 110, feedthrough pins 144, filter plates 150, ground pin 160, and antenna pin 162 may be pieced together and bonded physically and electrically as appropriate. The lend connectors 146, seals 148, and end seal 142 may be pieced together and placed into the recesses 188 and 190 of the connector enclosure body 112. The set screw block spacer 180 containing the set screw blocks may be placed into the recess 186 with rite feedthrough pins 144 corresponding to the set screw blocks being welded to the set screw blocks while the seals for the openings 114 may be inserted.

Prior to bringing the connector enclosure body 112 together with the connector enclosure base 110, the antenna cover 116 including the antenna support 184 the antenna conductor 183, and the antenna connecting pin 164 are pieced together an joined to the connector enclosure body 112. As discussed above, in tots example the antenna cover 116 slides onto the grooves 189 of the connector enclosure body 112 while the connecting pin 164 and related portion of the antenna cover 116 pass into the opening 194 of the connector enclosure body 112.

The connector enclosure base 110 is then mounted to the connector enclosure body 112 by sliding the connector enclosure base 110 transversely into position relative to the body 112 and then bonded the two such as by a metallic weld. In doing so, the feedthrough pins 144 move into contact with corresponding feedthrough plate passages while being accommodated by the recesses 192. Likewise, the antenna pin 162 moves into contact with the connecting pin 164 while the bottom of the antenna cover 116 slides into the slot 134 of the connector enclosure base 110. The feedthrough pins 144 may then be welded to the lead connectors 146 while the antenna pin 162 may be welded to the connecting pin 164.

The components within the cavity of the connector enclosure body 112 are complete. The panel 118 is then placed over the cavity and welded into place within the indention 168 of the connector enclosure body 112 which holds the end seal 142 and the set screw block spacer 180 into place and thereby assists in holding the lead connectors 146 and seals 148 in place within the cavity. The panel 118 is bonded to the connector enclosure body 112 and connector enclosure base 110, such as by a metallic weld to complete the assembly of the connector enclosure 108. A filler material such as liquid silicone rubber is injected within the cavity of the connector enclosure body 112 through a remaining passageway to fill the cavity and the passageway. The grommets may be installed and the seal 120 is poured into place.

One manner of assembling the medical device 102 may proceed as follows. The connector enclosure 108 is assembled as discussed above. The medical circuitry 152, coil assembly 154, battery 141, flexible circuit connector 170, and bumper 172 are pieced together and the exposed ends 156 of the feedthrough pins 144, ground pin 160, and antenna pin 162 are bonded to conductive pads 158 on the flexible circuit connector 170. The isolation cup 148 is then placed around the medical circuitry 152, coil assembly 154, battery 141 and flexible circuit connector 170, with the isolation cup 138 being fitted to the feet 140 of the connector enclosure base 110.

The isolation cup 138 and those items within the isolation cup 138 are deposited into the lop opening of the can 106. The isolation cup 138 and those items within the isolation cup 138 slide down into the can 106 until the bumper 172 contacts the bottom interior wall of the can 106. At that time, the top edge of the can 106 engages the lower edge 166 of the lip around the connector enclosure base 110. The top edge of the can 106 is then bonded at the point of contact to the connector enclosure base 110 such as by a metallic weld to complete the assembly of the medical device 102.

While embodiments have been particularly shown and described, it will be understood by those skilled in the art that various other changes in the form and details may be made therein without departing from the spirit and scope of the invention.

What is claimed is:

1. An implantable medical device comprising:
a can that houses medical circuitry;
a connector enclosure that includes an opening and a base, the base including a plurality of feedthrough pin passageways spaced longitudinally, the connector enclosure defining a cavity,
lead connectors within the cavity and aligned with the opening,
a plurality of feedthrough pins electrically connected to the lead connectors, each of the plurality of feedthrough pins passing through a respective one of the plurality of feedthrough pin passageways;
a ground pin at the base; and
a flex circuit extending within the can, the flex circuit including electrical contacts, each of the electrical contacts connected to a respective one of the plurality of feedthrough pins such that the flex circuit electrically connects the plurality of feedthrough pins and the medical circuitry, the flex circuit electrically connected to the ground pin to provide a ground connection for the medical circuitry.

2. The device of claim 1, wherein the ground pin is in electrical connection with the base, and wherein the base is in electrical connection with the can.

3. The device of claim 2, wherein the base comprises a metallic material, and wherein the can comprises a metallic material.

4. The device of claim 1, wherein the base further comprises a ground pin passageway, wherein the ground pin extends from the electrical connection to the flex circuit within the can to the ground pin passageway and terminates within the ground pin passageway, and wherein the plurality of feedthrough pins extend beyond the ground pin, through the opening of the connector enclosure, and to the respective lead connectors within the cavity of the connector enclosure.

5. The device of claim 4, wherein the ground pin passageway has a smaller cross-sectional area than each of the plurality of feedthrough pin passageways.

6. The device of claim 1, wherein each of the electrical contacts is electrically connected to the respective one of the plurality of feedthrough pins within the can, and wherein the flex circuit is electrically connected to the ground pin within the can.

7. The device of claim 6, wherein each of the electrical contacts is electrically connected to the respective one of the plurality of feedthrough pins and the flex circuit is electrically connected to the ground pin at a common elevation within the can.

8. The device of claim 1, further comprising:
an antenna pin at the base, the flex circuit electrically connected to the antenna pin such that the flex circuit electrically connects the antenna pin and the medical circuitry.

9. The device of claim 8, further comprising:
an antenna conductor at an antenna support, the antenna support extending along an outer portion of the connector enclosure opposite the base.

10. The device of claim 9, further comprising:
an antenna connecting pin that electrically connects the antenna pin to the antenna conductor, wherein the antenna connecting pin extends perpendicular to the antenna pin and toward a perimeter of the connector enclosure.

11. The device of claim 1, further comprising:
a filter plate adjacent the base, the filter plate including at least one conductive trace extending within the filter plate and electrically connected to at least one of the plurality of feedthrough pins.

12. The device of claim 11, wherein the filter plate include a ceramic material, wherein the at least one conductive trace extends through the ceramic material to an edge of the filter plate, and wherein the edge of the filter plate is electrically coupled to the base so that the at least one conductive trace is electrically coupled to the base.

13. The device of claim 11, wherein the filter plate includes a plurality of feedthrough pin passageways axially aligned with the plurality of feedthrough pin passageways of the base such that the plurality of feedthrough pins extend through the plurality of feedthrough pin passageways of the base and the plurality of feedthrough pin passageways of the filter plate in a parallel orientation.

14. The device of claim 13, wherein the at least one conductive trace is present at at least one of the plurality of feedthrough pin passageways of the filter plate such that at least one of the plurality of feedthrough pins is electrically connected to the at least one conductive trace at the at least one of the plurality of feedthrough pin passageways of the filter plate.

15. The device of claim 11, further comprising:
an antenna pin at the base, the flex circuit electrically connected to the antenna pin such that the flex circuit electrically connects the antenna pin and the medical circuitry, wherein the antenna pin is spaced apart from the filter plate.

16. An implantable medical device comprising:
a can that houses medical circuitry, the can defining a longitudinal axis;
a connector enclosure that includes an opening and a base, the connector enclosure defining a cavity, the base including a first group of a plurality of feedthrough pin passageways and a second group of a plurality of feedthrough pin passageways, the first group of the plurality of feedthrough pin passageways aligned on a first axis extending perpendicular to the longitudinal axis of the can and the second group of the plurality of feedthrough pin passageways aligned on a second axis, spaced apart from the first axis, extending perpendicular to the longitudinal axis of the can;
a first group of lead connectors within the cavity, wherein the first group of lead connectors are aligned with both the opening and the first group of the plurality of feedthrough pin passageways, and wherein the first group of lead connectors are offset from the second group of the plurality of feedthrough pin passageways;
a first group of lead connector seals disposed between the first group of lead connectors,
a first group of a plurality of feedthrough pins electrically connected to the first group of lead connectors, each of the first group of the plurality of feedthrough pins passing through a respective one of the first group of the plurality of feedthrough pin passageways;
a ground pin at the base; and
a flex circuit extending within the can, the flex circuit including electrical contacts, each of the electrical contacts connected to a respective one of the first group of the plurality of feedthrough pins such that the flex circuit electrically connects the first group of the plurality of feedthrough pins and the medical circuitry, the flex circuit electrically connected to the ground pin to provide a ground connection for the medical circuitry.

17. The device of claim 16, further comprising:
a second group of lead connectors within the cavity, wherein the second group of lead connectors are aligned with both the opening and the second group of the plurality of feedthrough pin passageways, and wherein the second group of lead connectors are offset from the first group of the plurality of feedthrough pin passageways.

18. The device of claim 17, further comprising:
a second group of a plurality of feedthrough pins electrically connected to the second group of lead connectors, each of the second group of the plurality of feedthrough pins passing through a respective one of the second group of the plurality of feedthrough pin passageways.

19. The device of claim 18, wherein each of the electrical contacts is connected to a respective one of the first group of the plurality of feedthrough pins and the second group of the plurality of feedthrough pins such that the flex circuit electrically connects the first group of the plurality of feedthrough pins and the second group of the plurality of feedthrough pins to the medical circuitry.

20. The device of claim 19, wherein the electrical contacts of the flex circuit include a first group of electrical contacts aligned longitudinally with the first axis and a second group of electrical contacts aligned longitudinally with the second axis such that the flex circuit electrically connects the first group of the plurality of feedthrough pins to the medical circuitry at a first position within the can that is offset in a direction perpendicular to the longitudinal axis of the can from a second position within the can at which the flex circuit electrically connects the second group of the plurality of feedthrough pins to the medical circuitry.

* * * * *